(12) United States Patent
Fischer et al.

(10) Patent No.: US 6,180,807 B1
(45) Date of Patent: Jan. 30, 2001

(54) DIRECT SYNTHESIS OF ORGANORHENIUM OXIDES FROM COMPOUNDS CONTAINING RHENIUM

(75) Inventors: Richard Walter Fischer, Bad Soden; Wolfgang Anton Herrmann, Freising; Roland Kratzer, Kriftel, all of (DE)

(73) Assignee: Aventis Research & Technologies GmbH & Co. KG, Frankfurt am Main (DE)

( * ) Notice: Under 35 U.S.C. 154(b), the term of this patent shall be extended for 0 days.

(21) Appl. No.: 09/403,439

(22) PCT Filed: Mar. 31, 1998

(86) PCT No.: PCT/EP98/01865

§ 371 Date: Feb. 10, 2000

§ 102(e) Date: Feb. 10, 2000

(87) PCT Pub. No.: WO98/47907

PCT Pub. Date: Oct. 29, 1998

(30) Foreign Application Priority Data

Apr. 24, 1997 (DE) .............................. 197 17 178

(51) Int. Cl.[7] .................................................. C07F 13/00
(52) U.S. Cl. ................................................................ 556/46
(58) Field of Search ................................. 556/46; 502/167

(56) References Cited

U.S. PATENT DOCUMENTS

| 5,155,247 | 10/1992 | Herrmann et al. ..................... 556/46 |
| 5,342,985 | 8/1994 | Herrmann et al. .................... 556/482 |

OTHER PUBLICATIONS

Chemical Abstracts, vol. 111, Abstract. No. 7580h, (1989).
Chemical Abstracts, vol. 107, Abstract. No. 198579q, (1987).
Chemical Abstracts, vol. 67, Abstract No. 288782, (1967).
Journal of Organomettalic Chemistry, 413 (1991), pp. 11–25.

*Primary Examiner*—Porfirio Nazario-Gonzalez
(74) *Attorney, Agent, or Firm*—Frommer Lawrence & Haug

(57) ABSTRACT

The present invention relates to a process for the preparation of organorhenium oxides from rhenium-containing compounds, where the rhenium-containing compound is reacted with a silylating agent and organylating reagent, and the rhenium-containing compound originates in particular from the residue from a spent organorhenium oxide catalyst or rhenium oxide catalyst.

8 Claims, No Drawings

DIRECT SYNTHESIS OF ORGANORHENIUM OXIDES FROM COMPOUNDS CONTAINING RHENIUM

The present invention comprises a novel process for preparing organorhenium oxides from rhenium-containing compounds, in particular from perrhenates, and the catalyst recycling, which is made possible for the first time, on use of organorhenium oxides in catalytic processes.

The first report on the parent compound of the organorhenum oxides, methyltrioxorhenium, was that in 1979 by I. A. Beattie et al. (I. A. Beattie, P. J. Jones, *Inorg. Chem.*, 18 (1979) 2318). It is produced in up to 50% yield by oxidation of tetramethylrhenium(VI) oxide $(CH_3)_4ReO$ or decomposition of trimethyldioxorhenium(VII) $(CH_3)_3ReO_2$, the starting compounds being exposed to dry air for some weeks in order to effect the oxidative conversion.

This is no longer a significant access route because the precursors are difficult to obtain and the synthesis is time-consuming. Instead, two alternative routes for synthesizing organorhenium(VII) oxides are currently in use and are essentially derived from the studies by J. G. Kuchler (Thesis, Munich TU) in 1987. Both processes are based on commercially available rhenium heptoxid $Re_2O_7$ as rhenium source. $Re_2O_7$ is highly moisture-sensitive so that the reactions must be carried out under protective gas and with dry solvents.

Direct alkylation (arylation) of rhenium heptoxide $Re_2O_7$ with nonreducing transfer reagents such as tetraalkyltin $SnR_4$ or dialkylzinc $ZnR_2$ leads, in smooth reactions, to the corresponding organorhenium oxides. The disadvantage of this method is that half of the rhenium results as polymeric trialkyl stannyl perrhenate or as zinc perrhenate. This means that the maximum yield which can theoretically be achieved is only 50% (based on rhenium). The yield actually achieved then is about 45%.

If the alkylation is carried out with mixed esters of perrhenic acid and carboxylic acids, these rhenium-containing byproducts can be avoided (W. A. Herrmann et al., *Inorg. Chem.*, 31 (1992) 4431). In this so-called anhydride route, rhenium heptoxide are reacted successively with carboxylic anhydrides (preferably trifluoroacetic anhydride) and tri (n-butyl)tin compounds. The yields in this case are 80–90%, although—if high purity is required—complete removal of the resulting tri(n-butyl)tin carboxylic anhydrides from the formed MTO is time-consuming and complicated. The described reaction is confined to less reactive tin compounds because the use of more reactive tin compounds gives only unsatisfactory results. Its synthetic scope is therefore very limited. In addition, it requires the use of relatively costly chemicals.

It was an object of the present invention to provide a novel process with which it is possible to obtain organorhenium oxides in a simple and low-cost manner in good yields.

This object is achieved by a process in which a rhenium-containing compound, where the rhenium-containing compound is perrhenate, is reacted with a silylating agent and an organylating agent to give the corresponding organorhenium oxide.

In a preferred embodiment, the invention relates to a process for preparing compounds of the formula (I)

$$R_aRe_bO_cL_d \qquad (I)$$

where a=an integer from 1 to 6
b=an integer from 1 to 4
c=an integer from 1 to 12
d=an integer from 0 to 4
L=a Lewis base ligand and the total of a, b and c is such as to comply with the penta- to heptavalency of rhenium, with the proviso that c is not greater than 3×b and in which R is identical or different, and is an aliphatic hydrocarbon radical having 1 to 40 and preferably from 1 to 20 carbon atoms, an aromatic hydrocarbon radical having 6 to 40 and preferably from 6 to 20 atoms or arylalkyl radical having 7 to 40 and preferably from 7 to 20 atoms, where the radical R can, where appropriate, be substituted identically or differently, independently of one another.

Examples of substituents are halogen, hydroxyl, alkoxy, aryloxy, alkylamino and arylamino, alkylphosphine, arylphosphine, alkylsulfonyl, arylsulfonyl, alkyl- and aryl (sulfonyl)phosphine.

The novel direct synthesis of organorhenium oxides from rhenium-containing compounds, especially perrhenates such as $MReO_4$, $M(ReO_4)_2$, dispenses with the disadvantages mentioned at the outset. Thus, methyltrioxorhenium (MTO) and other moisture-stable organorhenium oxides can be synthesized in good yields without the exclusion of air or moisture (see Table 1).

Suitable rhenium-containing compounds are, in particular, perrhenates such as, for example, $MReO_4$ and $M(ReO_4)_2$. M can be any suitable counterion. For example, M can be an ion from the group of alkali metal, alkaline earth metal or B group elements. Examples which may be mentioned are $AgReO_4$, $KReO_4$, $NaReO_4$, $Zn(ReO_4)_2$, $Ca(ReO_4)_2$, $(CH_3)_3SnReO_4$ or else $NH_4ReO_4$.

In another embodiment of the invention, the rhenium-containing compound originates from the catalyst residue from spent organorhenium oxide catalysts or from Re-containing solutions in general.

The reaction takes place in a one-pot reaction in organic solvents, in particular donor solvents (for example THF, acetonitrile).

The dissolved or suspended rhenium-containing compound is reacted with a silylating agent and an organylating agent.

In principle, any silylating agent which results in an appropriate reaction as shown in scheme 1 is suitable. A preferred silylating agent is chlorotrimethylsilane because it is easily obtainable. It is also possible to use other chloro-alkylsilanes such as chloro-tert-butyidimethylsilane etc. The amount of silylating agent should in general be at least equimolar relative to the rhenium-containing compound. However, an excess is preferred, and an amount corresponding to 2 to 2.5 equivalents is particularly advantageous.

It is also possible to select the organylating reagent and its amount as desired as long as an appropriate reaction as shown in Scheme 1 is ensured. Thus, the use of any organylating reagent known for such purposes is conceivable. Suitable examples of organylating reagents are the organometallic compounds of tin, zinc, aluminum, magnesium, lithium, copper, cadmium and mercury, and tin or zinc alkyls or aryls are preferred.

The amount of organylating reagent should, in a manner corresponding to the silylating agent, be approximately equimolar to the amount of rhenium-containing compound employed, an excess possibly being advantageous. The organylating reagent is preferably employed in an amount which corresponds to 1 to 1.5 equivalents based on the rhenium-containing compound.

If required, however, the organylating reagent can, like the silylating agent, be employed in smaller or larger amounts.

To react perrhenates of low solubility, such as potassium perrhenate $KReO_4$ or ammonium perrhenate $NH_4ReO_4$, it is advisable to add up to one equivalent of acid (usually sulfuric acid) in order to increase the solubility of the perrhenate, it also being possible for the amount of added acid to be more if required.

The use of zinc alkylating agents is also possible by in situ reaction of $ZnCl_2$ with the appropriate organolithium compound LiR or the appropriate Grignard compound RMgX (X=halide).

This novel synthetic strategy represents a low-cost and entirely unproblematical way (no inert gas atmosphere, no anhydrous solvents) of obtaining organorhenium oxides from a large number of starting materials.

As already mentioned, it is not in principle necessary according to the invention to ensure that the solvents used are anhydrous. However, it may be advantageous to use the usual laboratory dry solvents. Thus, it has emerged that the yield can be increased further in this way.

The reaction temperature for the process according to the invention can be chosen in a wide range from –100 to +110° C., in particular –78° C. to +80° C. However, the reaction normally takes place under moderate conditions, i.e. from room temperature to refluxing.

It is assumed that the reaction takes place via the following intermediates (scheme 1, example of methyltrioxorhenium). The following scheme serves merely for illustration.

W. A. Herrmann, J. Organomet. Chem., 500 (1995) 149): Aromatic oxidation (DE 4419799.3) Olefin isomerization and olefin metathesis (DE 4228887, DE 3940196, EP 891224370).

It is also possible to mention a number of other processes which can be catalyzed by methyltrioxorhenium, such as Baeyer-Villiger oxidation, Diels-Alder reaction, olefination of aldehydes and oxidation of metal carbonyls, sulfides and many other organic and inorganic substrates.

For further progress in the industrial utilization of organorhenium oxides, especially MTO, in the described processes, it is therefore, of course, crucially important that spent catalyst be recycled. Despite some organorhenium oxides, for example MTO and the peroxo complex, being relatively tolerant of water formed in the reaction, the predominant mechanism of catalyst deactivation is hydrolysis, which leads to elimination of the organic radical to form perrhenic acid which, after the work-up, finally ends in perrhenate salts.

It is possible with the aid of the process according to the invention for the perrhenates obtained from industrial processes to be subjected directly to catalyst regeneration. As an example, the recycling of the rhenium catalyst can be shown by the example of MTO-catalyzed aromatic oxidation:

The catalytic reaction normally takes place in acetic acid as solvent. After the reaction has taken place, the homogeneous system can be converted into a two-phase system by adding water and an organic solvent such as, for example,

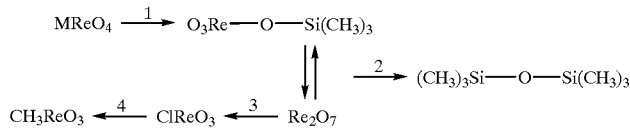

Scheme 1: Reaction mechanism for the formation of methyltrioxorhenium from perrhenates (1) Reaction of the perrhenate with one equivalent of chlorotrimethylsilane to give trimethylsilyl perrhenate (with formation of sparingly soluble chlorides=driving force of the reaction).
(2) Solvolysis of trimethylsilyl perrhenate to form rhenium heptoxide and hexamethyldisilazane.
(3) Cleavage of rhenium heptoxide with the second equivalent of chlorotrimethylsilane to give chlorotrioxorhenium and trimethylsilyl perrhenate.
(4) Alkylation of chlorotrioxorhenium with tetramethyltin to give methyltrioxorhenium and trimethyltin chloride.

An outstanding advantage of the novel synthetic method is also its use in catalyst recycling of exhausted reaction solutions. Organorhenium oxides (especially methyltrioxorhenium) can be employed as excellent catalysts in a wide variety of areas of organic synthesis. The lively research activity and the large number of patents in this area show how highly the industrial potential of these catalysts is regarded.

The most promising candidates for industrial use include MTO-catalyzed olefin epoxidation and MTO-catalyzed aromatic oxidation (U.S. Pat. No. 5,166,372, DE 39 02 357, EP 90101439.9). MTO is converted stepwise by hydrogen peroxide $H_2O_2$ via a mono(peroxo)- into a bis(peroxo)rhenium complex. The latter is a highly efficient catalyst for epoxidation of a wide range of olefin products.

In addition, the following MTO-catalyzed processes have to date been patented or described in the literature (review:

chloroform. After phase separation and, where appropriate, a washing step, the required oxidation product can be isolated from the organic phase, while the catalyst is precipitated from the aqueous phase as sparingly soluble potassium perrhenate $KReO_4$ for example by adding a potassium salt (preferably 1 to 3 equivalents of potassium chloride KCl or $K_2CO_3$).This perrhenate can be employed without any purification for the process according to the invention.

EXAMPLES

See also Table 1

1. 500 mg of $NaReO_4$ are suspended in 10 ml of acetonitrile and, after addition of 2.2 equivalents of chlorotrimethylsilane and 1.1 equivalents of tetramethyltin, refluxed for 4 h. The solution is then filtered to remove insoluble sodium chloride and is evaporated to dryness. Subsequent sublimation affords analytically pure methyltrioxorhenium in a yield of 70%.
2. 500 mg of $AgReO_4$ are dissolved in 10 ml of acetonitrile and, after addition of 2.2 equivalents of chlorotrimethylsilane and 1.1 equivalents of tetramethyltin, stirred at room temperature for 12 h. The solution is then filtered to remove insoluble silver chloride and is evaporated to dryness. Subsequent sublimation affords analytically pure methyltrioxorhenium in a yield of 76%.
3. 500 g of $KReO_4$ are suspended in 10 ml of acetonitrile and, after addition of 1 equivalent of concentrated sulfuric acid, 2.2 equivalents of chlorotrimethylsilane and 1.1 equivalents of tetramethyltin, stirred at room temperature for 24 h. The solution is then evaporated to dryness and extracted several times with pentane. The combined pentane extracts are concentrated and put in a cold place. The precipitated methyltrioxorhenium is filtered off and, where appropriate, also subjected to a sublimation. Methyltrioxorhenium is obtained in a yield of 70%.

4. 500 mg of $NH_4ReO_4$ are suspended in 10 ml of acetonitrile and, after addition of 1 equivalent of concentrated sulfuric acid, 2.2 equivalents of chlorotrimethylsilane and 1.1 equivalents of tetramethyltin, stirred at room temperature for 24 h. The solution is then evaporated to dryness and extracted several times with pentane. The combined pentane extracts are concentrated and put in a cold place. The precipitated methyltrioxorhenium is filtered off and, where appropriate, also subjected to a sublimation. Methyltrioxorhenium is obtained in a yield of 56%.

5. 500 mg of $NaReO_4$ are suspended in 10 ml of dry acetonitrile and, after addition of 2 equivalents of chlorotrimethylsilane and 1 equivalent of $Zn((CH_3)_2NC_3H_6)_2$, stirred at 0° C. for 12 h. The solution is then evaporated to dryness and put in a cold place. 3-[N,N-Dimethylamino-n-propyl]-trioxorhenium precipitates from the solution in a yield of 25%.

6. 9 g of $KReO_4$ are suspended in 150 ml of acetonitrile and, after the addition of 1 equivalent of concentrated sulfuric acid, 2.2 equivalents of chlorotrimethylsilane and 1.1 equivalents of tetramethyltin, stirred at room temperature for 24 h. The solution is then evaporated to dryness and put in a cold place. The precipitated methyltrioxorhenium is filtered off and, where appropriate, also subjected to a sublimation. Methyltrioxorhenium is obtained in a yield of 63%.

7. The examples listed in Table 1 were carried out in analogy to the foregoing examples.

TABLE 1

Synthesis of organorhenium oxides from perrhenates

| | Perrhenate | Alkylating agent | Conditions | $RReO_3$ yeild in %[1] |
|---|---|---|---|---|
| 1 | $AgReO_4$ | $(CH_3)_4Sn$ | $CH_3CN$, 12 h, RT | 76 |
| 2 | $Ca(ReO_4)_2$ | $(CH_3)_4Sn$ | $CH_3CN$, 4 h, Reflux. | 80 |
| 3 | $NaReO_4$ | $(CH_3)_4Sn$ | $CH_3CN$, 4 h, Reflux. | 70 |
| 4 | $KReO_4$ | $(CH_3)_4Sn$ | $CH_3CN$, 4 h, Reflux. | 53 |
| 5 | $KReO_4$ | $(CH_3)_4Sn$ | $CH_3CN$, 24 h, RT | 70 |
| 6 | $NH_4ReO_4$ | $(CH_3)_4Sn$ | $CH_3CN$, 4 h, Reflux. | 43 |
| 7 | $NH_4ReO_4$ | $(CH_3)_4Sn$ | $CH_3CN$, 24 h, RT | 56 |
| 8 | $Me_3SnReO_4$ | $(CH_3)_4Sn$ | $CH_3CN$, 24 h, RT | 85[2] |
| 9 | $Zn(ReO_4)_2$ | $(CH_3)_4Sn$ | $CH_3CN$, 2 h, Reflux. | 72 |
| 10 | $NaReO_4$ | $Bu_3SnCH_3$ | $CH_3CN$, 4 h, Reflux. | 46 |
| 11 | $AgReO_4$ | $ZnEt_2$ | $CH_3CN$, 12 h, 0° C. | 37[2] |
| 12 | $NaReO_4$ | $Zn((CH_3)_2NC_3H_6)_2$ | $CH_3CN$, 12 h, 0° C. | 25 |

[1]isolated yield apart from indicated Examples 8 and 11
[2]GC yield (+/−5%)

What is claimed is:

1. A process for the preparation of organorhenium oxides from rhenium-containing compounds, where the rhenium-containing compound is reacted with a silylating agent and an organylating reagent.

2. The process as claimed in claim 1, where the organorhenium oxide is a compound of the formula (I)

$$R_a Re_b O_c L_d \qquad (I)$$

where a=an integer from 1 to 6 b=an integer from 1 to 4 c=an integer from 1 to 12 d=an integer from 0 to 4

L=a Lewis base ligand and the total of a, b and c is such as to comply with the penta- to heptavalency of rhenium, with the proviso that c is not greater than 3×b and in which R is identical or different, and is an aliphatic hydrocarbon radical having 1 to 20 carbon atoms, an aromatic hydrocarbon radical having 6 to 20 atoms or arylalkyl radical having 7 to 20 atoms, where the radical R can, where appropriate, be substituted identically or differently, independently of one another.

3. The process as claimed in claim 1, where the rhenium-containing compound is a perrhenate.

4. The process as claimed in claim 3, where the perrhenate is $MReO_4$ or $M(ReO_4)_2$, and M is selected from the alkali metal or alkaline earth metal elements, the B group elements or an ammonium.

5. The process as claimed in claim 1, where the silylating agent is a chloroalkylsilane.

6. The process as claimed in claim 1, where the organylating reagent is an organometallic compound of tin, zinc, aluminum, magnesium, lithium, copper, cadmium or mercury.

7. The process as claimed in claim 1, where the rhenium-containing compound is obtained from a spent organorhenium oxide or/and rhenium oxide catalyst or/and from a solution containing a rhenium compound, rhenium complex ions or/and rhenium ions.

8. The process as claimed in claim 7, where the spent organorhenium oxide or rhenium oxide catalyst is obtained as potassium perrhenate.

* * * * *